US010980333B2

(12) United States Patent
Bauer et al.

(10) Patent No.: US 10,980,333 B2
(45) Date of Patent: Apr. 20, 2021

(54) COSMETIC PRODUCT COMPRISING A METAL CAN, AND THE CONTENTS OF SAME

(71) Applicant: BEIERSDORF AG, Hamburg (DE)

(72) Inventors: Anja Bauer, Hamburg (DE); Volker Kallmayer, Hamburg (DE); Peter Steidle, Hamburg (DE); Klaus-Peter Stange, Wentorf (DE)

(73) Assignee: BEIERSDORF AG, Hamburg (DE)

( * ) Notice: Subject to any disclaimer, the term of this patent is extended or adjusted under 35 U.S.C. 154(b) by 254 days.

(21) Appl. No.: 15/551,597

(22) PCT Filed: Feb. 8, 2016

(86) PCT No.: PCT/EP2016/052613
§ 371 (c)(1),
(2) Date: Aug. 17, 2017

(87) PCT Pub. No.: WO2016/134963
PCT Pub. Date: Sep. 1, 2016

(65) Prior Publication Data
US 2018/0035784 A1 Feb. 8, 2018

(30) Foreign Application Priority Data

Feb. 27, 2015 (DE) .......................... 102015203566.2

(51) Int. Cl.
*A45D 40/00* (2006.01)
*A61K 8/34* (2006.01)
*A61K 8/06* (2006.01)
*A45D 33/00* (2006.01)
*A45D 34/00* (2006.01)
*A61K 8/35* (2006.01)
*A61Q 19/00* (2006.01)
*A61K 8/9789* (2017.01)
*A61K 8/9794* (2017.01)
*A61K 8/31* (2006.01)
*A61K 8/36* (2006.01)
*A61K 8/891* (2006.01)
*A61Q 17/04* (2006.01)
*B65D 25/14* (2006.01)
*B65D 43/02* (2006.01)

(52) U.S. Cl.
CPC ....... *A45D 40/0068* (2013.01); *A45D 33/003* (2013.01); *A45D 34/00* (2013.01); *A61K 8/06* (2013.01); *A61K 8/31* (2013.01); *A61K 8/34* (2013.01); *A61K 8/345* (2013.01); *A61K 8/35* (2013.01); *A61K 8/361* (2013.01); *A61K 8/891* (2013.01); *A61K 8/9789* (2017.08); *A61K 8/9794* (2017.08); *A61Q 17/04* (2013.01); *A61Q 19/00* (2013.01); *B65D 25/14* (2013.01); *B65D 43/0231* (2013.01); *A61K 2800/87* (2013.01)

(58) Field of Classification Search
CPC .. A45D 40/0068; A45D 33/003; A45D 34/00; A61K 8/9794; A61K 8/9789; A61K 8/06; A61K 8/31; A61K 8/34; A61K 8/345; A61K 8/35; A61K 8/361; A61K 8/891; A61K 2800/87; A61Q 17/04; A61Q 19/00
See application file for complete search history.

(56) References Cited

U.S. PATENT DOCUMENTS

| 5,496,565 | A | 3/1996 | Heinze et al. |
| 7,544,366 | B1* | 6/2009 | Lutz ...................... A61K 8/365 424/401 |
| 2003/0209566 | A1 | 11/2003 | Winckels |
| 2004/0057921 | A1* | 3/2004 | Walsh .................... A61K 8/044 424/70.11 |
| 2007/0014744 | A1 | 1/2007 | Swistowski et al. |
| 2010/0287891 | A1* | 11/2010 | Lee ..................... B05B 11/0021 53/473 |
| 2012/0315315 | A1 | 12/2012 | Neubourg |
| 2013/0273274 | A1 | 10/2013 | Mueller et al. |

(Continued)

FOREIGN PATENT DOCUMENTS

| DE | 4308282 A1 | 9/1994 |
| DE | 102005033520 A1 | 1/2007 |

(Continued)

OTHER PUBLICATIONS

International Journal of Toxicology, "Final Report on the Safety Assessment of Hydrogenated Cottonseed Oil, Cottonseed (Gossypium) Oil, Cottonseed Acid, Cottonseed Glyceride, and Hydrogenated Cottonseed Glyceride", 20(Suppl. 2):21-29, 2001.*
Anonymous: "GNPD—Cream" Nov. 1, 2014 (Nov. 1, 2014). Retrieved from the Internet: URL:http://www.gnpd.com/sinatra/recordpage/2783849/from search/mbquipw1zH/ [retrieved on—Apr. 6, 2016].
Anonymous: "GNPD—Moisturising Cream" Sep. 1, 2014 (Sep. 1, 2014). Retrieved from the Internet: URL:http://www.gnpd.com/sinatra/recordpage/2693945/from search/dBH42FWGp4/ [retrieved on—Apr. 6, 2016].

(Continued)

*Primary Examiner* — Genevieve S Alley
(74) *Attorney, Agent, or Firm* — Abel Schillinger, LLP

(57) ABSTRACT

Disclosed is a cosmetic product comprising a metal can which comprises a metal container (A) which has a rotary thread (A') and contains a cosmetic preparation as well as a lid (D) having a thread (D') and being of the same metal as the container. The lid can be screwed onto/unscrewed from the container by means of threads (D') and (A') via rotational movement. The cosmetic preparation comprises an emulsion of one or more hydrophilic phases and one or more lipophilic phases. The one or more lipophilic phases comprise at least one lipid having a spreading coefficient at 25° C. of no more than 700 mm²/10 minutes, at least one lipid having a dropping point of >30° C., and at least one monovalent and/or polyvalent alcohol in a total amount of at least 3 wt. %.

20 Claims, 2 Drawing Sheets

(56) References Cited

U.S. PATENT DOCUMENTS

| | | | | |
|---|---|---|---|---|
| 2014/0364509 A1* | 12/2014 | Wegner | .................... | A61K 8/34 |
| | | | | 514/724 |
| 2015/0038592 A1 | 2/2015 | Von Der Fecht et al. | | |
| 2015/0044157 A1* | 2/2015 | Kulkarni | ................ | A61K 8/602 |
| | | | | 424/70.22 |

FOREIGN PATENT DOCUMENTS

| | | | |
|---|---|---|---|
| DE | 102006035042 A1 | 1/2008 | |
| DE | 102010062807 A1 | 6/2012 | |
| DE | 202012005442 U1 | 7/2012 | |
| EP | 2363108 A1 | 9/2011 | |
| WO | 2013120829 A2 | 8/2013 | |

OTHER PUBLICATIONS

Anonymous: "GNPD—Strawberry Lip Care SPF 10" Aug. 1, 2013 (Aug. 1, 2013). Retrieved from the Internet: URL: ttp://www.gnpd.com/sinatra/recordpage/2157509/from searchjoBON4fFQnu/ [retrieved on—Apr. 6, 2016].

Anonymous: GNPD—Creme—Face and Neck Cream Jan. 1, 2015 (Jan. 1, 2015). Retrieved from the Internet: URL:http://www.gnpd.com/sinatra/recordpage/2902463/from searchbjUQcE9WAB/ [retrieved on—Apr. 6, 2016].

* cited by examiner

COSMETIC PRODUCT COMPRISING A METAL CAN, AND THE CONTENTS OF SAME

BACKGROUND OF THE INVENTION

1. Field of the Invention

The invention relates to a cosmetic product comprising a metal can composed of a container part with rotation thread (container thread), in the interior of which a cosmetic preparation is kept, and also a lid part made of metal with a thread (lid thread), wherein the lid part is unscrewable and screwable onto the container part in a closing manner by means of the lid thread and the container thread via rotational movement, i.e., designed to be openable and recloseable via a screw closure.

2. Discussion of Background Information

Cosmetic products comprising metal cans having contents, for example creams, fats and the like, have been used for at least a hundred years.

These known tin cans are disadvantageous in that either the choice of the wall material is limited, since screwing movement of the lid on the container part almost inevitably results in abrasion, which leads to unsightly signs of soiling, or containers without screw threads have to be chosen, which, however, can lead to leakage problems.

SUMMARY OF THE INVENTION

It is an object of the invention to provide a metal can having a profile edge which has a circular plane-surface and is especially suitable for sealing and, at the same time, does not exhibit the described disadvantages of the prior art.

These objects are achieved according to the invention by a cosmetic product comprising a metal can comprising
aa) a metallic container part (A) with rotation thread (A'),
   aaa) in the interior of which a cosmetic preparation (Z) is present,
and also
bb) a lid part (D) with a thread (D') made of the same metal as the container part,
wherein the lid part (D) is unscrewable and screwable onto the container part (A) in a closing manner by means of the lid thread (D') and the container thread (A') via rotational movement, i.e., designed to be openable and reclosable via screwing movement,
   characterized in that the cosmetic preparation comprises an emulsion of
cc) one or more hydrophilic phases
dd) one or more lipophilic phases,
wherein
ee) in which the lipid phase contains at least one lipid which has a spreading value of at most 700 mm$^2$/10 minutes (at 25° C.),
ff) which further contains at least one lipid having a dropping point >30° C.,
gg) which further contains at least one monohydric and/or polyhydric alcohol in a proportion of, in total, at least 3% by weight, based on the total weight of the preparation (Z).
Advantageously, the preparation (Z) contains up to 20% by weight of lipophilic substances, of which the weight ratios of the components ee) to ff) expediently vary in the range between 20 to 80 to 50 to 50, preferably between 30 to 70 to 45 to 55.

Spreading is the property of low-viscosity oils, which property is often desired, though also often undesired in other situations, and is predominantly based on capillary forces, to be particularly easily distributed as a thin layer on substrates or else on the skin. This may be advantageous in skincare. This property may have a disadvantageous effect in the packaging of such oils or preparations containing said oils. A measure of spreading capacity is the spreading coefficient, which, for example, assumes particularly high values in defoamers and foam inhibitors.

Barry and Grace developed a method for determining spreading behavior (J. Pharmac. Sci. 61, 335 [1972] and Beyer developed a model test system for testing spreading behavior (Arch. Pharm. [Weinh.] 310, 729 [1977]; Chem. Abstr. 88, No. 12-79017 [1978]). Beyer further reports on the model-based spreading of ointments in Arch. Pharm. 310, 473 and 858 (1977); Zbl. Pharm. 118, 51 (1979). Pascale et. al. report on the spreading capacity of various liquid excipients based on fats or fat-like substances (Cosmet. Toiletries 100, No. 10, 75 [1985]).

The measurement unit of the spreading coefficient is that of the quotient formed from the spreading surface, across which the spreading takes place, and the spreading time, within which the spreading takes place. It is usually specified in [mm$^2$/10 minutes].

Within the context of the present disclosure, the expression "lipids" is occasionally used as an umbrella term for fats, oils, waxes and the like, as is thoroughly familiar to a person skilled in the art. The terms "oil phase" and "lipid phase" are also used synonymously.

A metal can that is advantageous according to the invention has a sufficiently broad, planar surface on the upper edge for sealing, meaning that overlays can be firmly sealed onto the can in a manner known per se.

To this end, a flexible film composed of metal, plastic or their composite, for example, is sealed onto the filled can by means of heat sealing or ultrasound, the inner protective coating applied before the shaping of the can having thermoplastically sealable or ultrasound-weldable properties.

It is also possible to subsequently apply a suitable sealing material, such as high-melting-point wax, adhesive, coating or the like, to the annular plane-surface of the profile edge of the final-shape can, onto which the film is sealed, for example by pressure, heat, thermal radiation, ultrasound or the like, it also being possible to use a combination of these measures, as is part of the prior art. The sealed can can then be closed with a lid in a customary manner.

Advantageously, an inner protective lining, composed especially of a sealable coating or the like, is applied to the inner side of the can in a manner known per se, said inner protective lining advantageously already being applied before the shaping of the can and the rolled edge. According to a preferred embodiment, a bead runs laterally around the can, which bead serves for the stiffening of said can and possibly as a stop for a lid to be fitted, as is known per se. Further beads or other beads can be provided in a manner known per se. Moreover, the base of the can according to the invention is advantageously slightly inwardly curved, but can also be planar if desired.

Aluminum or an aluminum alloy is advantageously used as material for the can according to the invention, though also suitable is sheet steel that has been surface-treated, such as tin-plated, chrome-plated, aluminized, finished, plastics-coated, etc.

The cans according to the invention can be produced in a manner known per se.

The cosmetic or dermatological preparations according to the invention can be composed as is customary and can serve for the treatment, the care and the cleansing of skin and/or of hair and as makeup product in decorative cosmetics. They contain preferably from 0.001% by weight to 10% by weight, preferably from 0.05% by weight to 5% by weight, especially from 0.1-2.0% by weight, based on the total weight of the preparations, of active-ingredient combinations used according to the invention.

For use, the cosmetic or dermatological preparations are, according to the invention, applied in a sufficient amount to skin and/or hair in the manner customary for cosmetics.

Cosmetic and dermatological preparations according to the invention can be present in various forms. For example, they can be a solution, an anhydrous preparation, a water-in-oil (W/O) or oil-in-water (O/W) emulsion or microemulsion, a multiple emulsions, for example a water-in-oil-in-water (W/O/W) emulsion, a gel, a solid stick, an ointment or else an aerosol. It is also advantageous to administer isoquercitrin in encapsulated form, for example encapsulated in collagen matrices and other customary encapsulation materials, for example as cellulose encapsulations, in gelatin, wax matrices or liposomally. Wax matrices in particular, as described in DE-OS 43 08 282, have been found to be favorable.

It is also possible and advantageous in the context of the present invention to include active-ingredient combinations used according to the invention in aqueous systems or surfactant preparations for the cleansing of skin and of hair.

The cosmetic and dermatological preparations according to the invention can contain cosmetic excipients, as are customarily used in such preparations, for example preservatives, bactericides, perfumes, antifoams, dyes, pigments having a coloring action, thickeners, surface-active substances, emulsifiers, emollients, moisturizers and/or humectants, fats, oils, waxes or other customary constituents of a cosmetic or dermatological formulation such as alcohols, polyols, polymers, foam stabilizers, electrolytes, organic solvents or silicone derivatives.

Emulsions according to the invention are advantageous and contain, for example, the aforementioned fats, oils, waxes and other fatty materials, and also water and an emulsifier, as is customarily used for this type of formulation.

The lipid phase can advantageously be selected from the following group of substances:
  mineral oils, mineral waxes
  oils, such as triglycerides of capric acid or of caprylic acid, ester oils, such as dicaprylyl ether, also natural oils such as, for example, castor oil;
  fats, waxes and other natural and synthetic fatty materials, preferably esters of fatty acids with alcohols of low carbon number, for example with isopropanol, propylene glycol or glycerol, or esters of fatty alcohols with alkanoic acids of low carbon number or with fatty acids, or natural waxes, such as shea butter;
  alkyl benzoates;
  silicone oils such as dimethicones, dimethylpolysiloxanes, diethylpolysiloxanes, diphenylpolysiloxanes and also mixed forms thereof.

The oil phase of the emulsions, oleogels and hydrodispersions or lipodispersions within the context of the present invention is advantageously selected from the group of esters of saturated and/or unsaturated, branched and/or unbranched alkanecarboxylic acids of a chain length of from 3 to 30 carbon atoms and saturated and/or unsaturated, branched and/or unbranched alcohols of a chain length of from 3 to 30 carbon atoms, from the group of esters of aromatic carboxylic acids and saturated and/or unsaturated, branched and/or unbranched alcohols of a chain length of from 3 to 30 carbon atoms. Such ester oils can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and also synthetic, semisynthetic and natural mixtures of such esters, for example jojoba oil.

Furthermore, the oil phase can advantageously be selected from the group of branched and unbranched hydrocarbons and hydrocarbon waxes, of silicone oils, of dialkyl ethers, the group of saturated or unsaturated, branched or unbranched alcohols, and also of fatty acid triglycerides, particularly of triglycerol esters of saturated and/or unsaturated, branched and/or unbranched alkanecarboxylic acids of a chain length of from 8 to 24, especially 12-18, carbon atoms. For example, the fatty acid triglycerides can advantageously be selected from the group of synthetic, semisynthetic and natural oils, for example olive oil, sunflower oil, soybean oil, peanut oil, rapeseed oil, almond oil, palm oil, coconut oil, palm kernel oil and so on.

Any desired mixtures of such oil and wax components can advantageously be used too within the context of the present invention. It may also be advantageous to use waxes, for example cetyl palmitate, as sole lipid component of the oil phase.

Mixtures of $C_{12-15}$-alkyl benzoate and 2-ethylhexyl isostearate, mixtures of $C_{12-15}$-alkyl benzoate and isotridecyl isononanoate and also mixtures of $C_{12-15}$-alkyl benzoate, 2-ethylhexyl isostearate and isotridecyl isononanoate are particularly advantageous.

The hydrocarbons which can advantageously be used within the context of the present invention are paraffin oil, squalane and squalene.

Advantageously, the oil phase can further comprise a content of cyclic or linear silicone oils or consist entirely of such oils, though preference is given to using, besides the silicone oil or silicone oils, an additional content of other oil-phase components.

Advantageously, dimethicone is used as the silicone oil to be used according to the invention. But other silicone oils too can advantageously be used within the context of the present invention, for example hexamethylcyclotrisiloxane, polydimethylsiloxane, poly(methylphenylsiloxane).

Preferably, preparations according to the invention contain up to 35% by weight of a lipid phase, based on the total weight of the preparation (Z).

Particularly advantageously, the lipids used according to the invention are selected from the group of the following substances: palmitic acid, stearic acid, myristic acid, arachidonic acid, oleic acid, glyceryl stearate, cetyl alcohol, stearyl alcohol, hydrogenated coconut fatty acid glycerides, cera microcristallina, paraffinum liquidum, dimethicone.

The aqueous phase of the preparations according to the invention contains at least 3% by weight, preferably at least 5% by weight, particularly preferably at least 10% by weight, based on the total weight of the preparation (Z), of one or more alcohols, diols or polyols of low carbon number, and also optionally the ethers thereof, preferably ethanol, isopropanol, propylene glycol, glycerol, ethylhexylglycerin, the ethylene glycol, ethylene glycol monoethyl or monobutyl ether, propylene glycol monomethyl, monoethyl or monobutyl ether, diethylene glycol monomethyl or monoethyl ether and analogous products, also alcohols of low carbon number, for example ethanol, isopropanol, 1,2-propanediol, glycerol, and also especially one or more thickeners, which can advantageously be selected from the group silicon dioxide, aluminum silicates, polysaccharides and the derivatives thereof, for example hyaluronic acid, xanthan gum, hydroxypropylmethylcellulose, particularly advantageously from the group of polyacrylates, preferably a polyacrylate from the group of so-called Carbopols, for example the Carbopol types 980, 981, 1382, 2984, 5984, TR2, TR1 on their own or in combination.

In particular, mixtures of the aforementioned solvents are used. In the case of alcoholic solvents, water can be a further constituent.

Emulsions according to the invention are advantageous and contain, for example, the aforementioned fats, oils, waxes and other fatty materials, and also water and an emulsifier, as is customarily used for this type of formulation.

Gels according to the invention customarily contain alcohols of low carbon number, for example ethanol, isopropanol, 1,2-propanediol, glycerol, and water and/or an aforementioned oil in the presence of a thickener, which is preferably silicon dioxide or an aluminum silicate in the case of oily/alcoholic gels and preferably a polyacrylate in the case of aqueous/alcoholic or alcoholic gels.

Advantageously, preparations according to the invention can also contain further substances which absorb UV radiation in the UVA and/or UVB region, the total amount of the filter substances being, for example, from 0.1% by weight to 30% by weight, preferably from 0.5 to 10% by weight, especially from 1.0 to 6.0% by weight, based on the total weight of the preparations, in order to provide cosmetic preparations which protect hair and/or skin from the entire range of ultraviolet radiation.

BRIEF DESCRIPTION OF THE DRAWINGS

In the accompanying drawings.

DETAILED DESCRIPTION OF EMBODIMENTS OF THE INVENTION

The following examples are intended to describe the invention in more detail:

|  | Example 1 | Example 2 | Example 4 | Example 6 | Example 7 |
| --- | --- | --- | --- | --- | --- |
| Palmitic acid + stearic acid + myristic acid + arachidic acid + oleic acid | 2.2 | 0.9 | 2.4 | 3 | 1 |
| Glyceryl stearate | 1.2 | 0.85 | 1.4 | 9 | 1.2 |
| Cetyl alcohol | 1.2 | 1 | 1.4 | 9 | 1.2 |

-continued

|  | Example 1 | Example 2 | Example 4 | Example 6 | Example 7 |
| --- | --- | --- | --- | --- | --- |
| Stearyl alcohol | 1.2 |  | 1.4 | 2 |  |
| Hydrogenadted coco-glycerides | 1.2 |  | 1.4 | 2 |  |
| Cera microcristallina + paraffinum liquidum | 1.7 |  | 1.9 | 2.5 |  |
| Dimethicone | 0.75 | 0.25 | 0.75 | 0.75 | 0.25 |
| Paraffinum liquidum | 3 |  | 4 | 5 |  |
| Isopropyl stearate |  | 2.9 |  |  | 3.1 |
| Carbomer | 0.3 | 0.7 | 0.3 | 0.3 | 0.7 |
| Acrylates/C10-30 alkyl acrylate crosspolymer |  | 0.04 |  |  | 0.06 |
| Glycerol | 10 | 10 | 10 | 10 | 5 |
| Phenoxyethanol | 0.5 | 0.25 | 0.5 | 0.5 | 0.25 |
| Alcohol denat. 96% | 3 | 10 | 3 | 3 | 10 |
| Distarch phosphate |  | 0.5 |  |  | 1.5 |
| Methylparaben | 0.15 |  | 0.15 | 0.15 |  |
| Water + NaOH (45%) | 0.45 | 0.65 | 0.6 | 1 | 0.85 |
| Water | to 100 | to 100 | to 100 | to 100 | to 100 |

Figure 1:
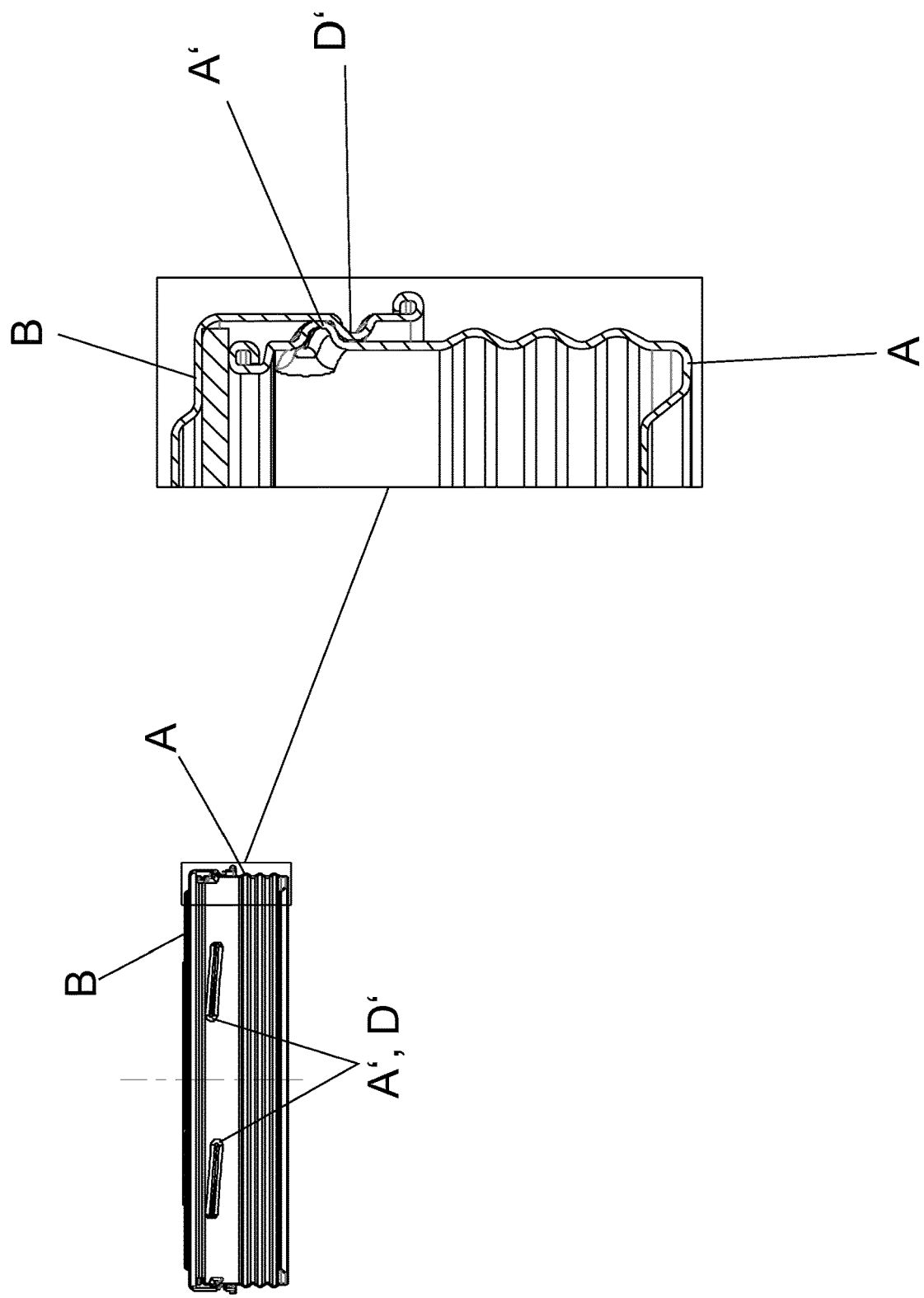
FIG. 1 shows a sectional drawing of a metal can in accordance with the present Invention and one detail of the wall of the can and of the lid.
Figure 3:
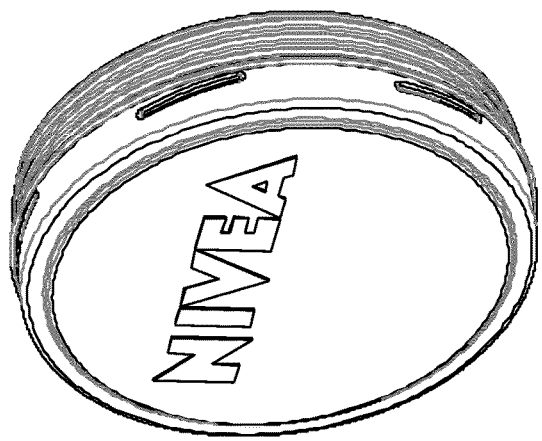
FIG. 3 shows a perspective drawing of the cosmetic product with commercial lettering.
Figure 2:
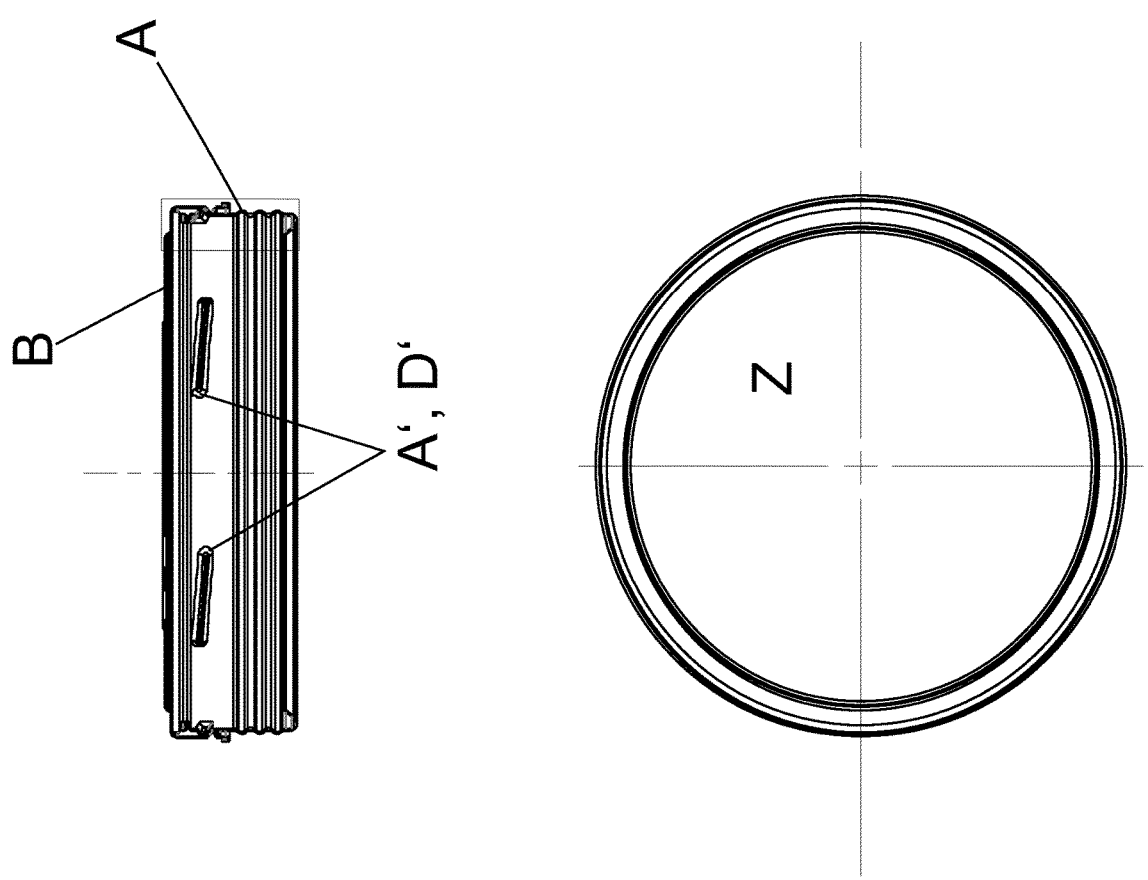
FIG. 2 shows the sectional drawing from FIG. 1 and a horizontal cut through the complete cosmetic product.

The preparations according to the examples are filled into aluminum cans according to FIGS. 1-3.

FIG. 1 shows a sectional drawing of a metal can used according to the invention, comprising aa) a metallic container part (A) with rotation thread (A'),
   aaa) in the interior of which a cosmetic preparation (Z) is present,
and also
bb) a lid part (D) with a thread (D') made of the same metal as the container part,
   wherein the lid part (D) is unscrewable and screwable onto the container part (A) in a closing manner by means of the lid thread (D') and the container thread (A') via rotational movement, i.e., designed to be openable and reclosable via screwing movement.

Furthermore, in FIG. 1 one detail of the wall of the can and of the lid, where especially thread parts A' and D' are singled out.

FIG. 2 shows the sectional drawing from FIG. 1 again and a horizontal cut through the complete cosmetic product, i.e., the can having the cosmetic preparation (Z).

FIG. 3 shows a perspective drawing of the cosmetic product with commercial lettering.

What is claimed is:

1. A cosmetic product, wherein the product comprises a metal can which comprises a metallic container (A) containing a cosmetic preparation (Z) and comprising a rotation thread (A') and a lid (D) having a thread (D') and being made of the same metal as the container (A), lid (D) being unscrewable and screwable onto container (A) in by thread (D') and thread (A') via rotational movement, and wherein the cosmetic preparation (Z) comprises an emulsion of one or more hydrophilic phases and one or more lipophilic phases and up to 20% by weight of lipophilic substances, based on a total weight of the preparation, the one or more lipophilic phases comprising, in a total concentration of at least 3% by weight, based on the total weight of the preparation, (i) at least one lipid having a spreading value at 25° C. of at least 700 mm$^2$/10 minutes, (ii) at least one lipid having a dropping point >30° C., and (iii) at least one monohydric and/or polyhydric alcohol.

2. The cosmetic product of claim 1, wherein the lipids (i) and (ii) are selected from palmitic acid, stearic acid, myristic acid, arachidonic acid, oleic acid, glyceryl stearate, cetyl alcohol, stearyl alcohol, hydrogenated coconut fatty acid glycerides, cera microcristallina, paraffinum liquidum, and dimethicone.

3. The cosmetic product of claim 1, wherein a weight ratio lipid (i) to lipid (ii) is from 20:80 to 50:50.

4. The cosmetic product of claim 1, wherein a weight ratio lipid (i) to lipid (ii) is from 30:70 to 45:55.

5. The cosmetic product of claim 1, wherein the preparation further comprises one or more UV filter substances.

6. The cosmetic product of claim 1, wherein the metal can consists of aluminum.

7. The cosmetic product of claim 6, wherein a protective lining is present on an inner side of the can.

8. The cosmetic product of claim 1, wherein the preparation comprises from 5% to 10% by weight of glycerol, based on a total weight of the preparation.

9. The cosmetic product of claim 1, wherein the preparation comprises from 2.9% to 9.6% by weight of ethanol, based on a total weight of the preparation.

10. The cosmetic product of claim 1, wherein the preparation comprises palmitic acid, stearic acid, myristic acid, arachidonic acid, and oleic acid.

11. The cosmetic product of claim 10, wherein the preparation further comprises glyceryl stearate, cetyl alcohol and dimethicone.

12. The cosmetic product of claim 1, wherein the preparation comprises hydrogenated coconut fatty acid glycerides.

13. The cosmetic product of claim 1, wherein the preparation comprises cera microcristallina.

14. The cosmetic product of claim 1, wherein the preparation comprises paraffinum liquidum.

15. The cosmetic product of claim 1, wherein the preparation comprises glyceryl stearate, cetyl alcohol and dimethicone.

16. A cosmetic product, wherein the product comprises a metal can which comprises a metallic container (A) containing a cosmetic preparation (Z) and comprising a rotation thread (A') and a lid (D) having a thread (D') and being made of the same metal as the container (A), lid (D) being unscrewable and screwable onto container (A) in by thread (D') and thread (A') via rotational movement, and wherein the cosmetic preparation (Z) comprises an emulsion of one or more hydrophilic phases and one or more lipophilic phases and comprises cera microcristallina, the one or more lipophilic phases comprising, in a total concentration of at least 3% by weight, based on a total weight of the preparation, (i) at least one lipid having a spreading value at 25° C. of at least 700 mm$^2$/10 minutes, (ii) at least one lipid having a dropping point >30° C., and (iii) at least one monohydric and/or polyhydric alcohol.

17. The cosmetic product of claim 16, wherein the lipids (i) and (ii) are selected from palmitic acid, stearic acid, myristic acid, arachidonic acid, oleic acid, glyceryl stearate, cetyl alcohol, stearyl alcohol, hydrogenated coconut fatty acid glycerides, cera microcristallina, paraffinum liquidum, and dimethicone.

18. The cosmetic product of claim 16, wherein the preparation further comprises one or more UV filter substances.

19. The cosmetic product of claim 16, wherein the preparation comprises from 5% to 10% by weight of glycerol, based on a total weight of the preparation.

20. The cosmetic product of claim 16, wherein the preparation comprises from 2.9% to 9.6% by weight of ethanol, based on a total weight of the preparation.

\* \* \* \* \*